United States Patent
Nolte et al.

(10) Patent No.: US 8,203,784 B2
(45) Date of Patent: Jun. 19, 2012

(54) MULTISPECTRAL LIGHTING APPARATUS

(75) Inventors: Andreas Nolte, Rosdorf (DE); Matthias Kramer, Goettingen (DE); Michael Brehm, Sulzbach-Laufen (DE); Christian Boeker, Gleichen (DE)

(73) Assignee: Carl Zeiss MicroImaging GmbH, Jena (DE)

( * ) Notice: Subject to any disclaimer, the term of this patent is extended or adjusted under 35 U.S.C. 154(b) by 441 days.

(21) Appl. No.: 12/445,132

(22) PCT Filed: Oct. 6, 2007

(86) PCT No.: PCT/EP2007/008693
§ 371 (c)(1),
(2), (4) Date: May 20, 2009

(87) PCT Pub. No.: WO2008/043500
PCT Pub. Date: Apr. 17, 2008

(65) Prior Publication Data
US 2010/0014157 A1 Jan. 21, 2010

(30) Foreign Application Priority Data
Oct. 11, 2006 (DE) .......................... 10 2006 048 054

(51) Int. Cl.
*G02B 21/06* (2006.01)
*F21V 9/00* (2006.01)
(52) U.S. Cl. ....................................... 359/385; 362/293
(58) Field of Classification Search .................. 359/385, 359/388; 362/293
See application file for complete search history.

(56) References Cited

U.S. PATENT DOCUMENTS

| 4,361,377 A * | 11/1982 | Pullen ........................... 359/385 |
| 6,388,807 B1 | 5/2002 | Knebel et al. |
| 7,042,638 B2 * | 5/2006 | Gonschor et al. ............. 359/385 |
| 2002/0121610 A1 | 9/2002 | Tewes et al. |
| 2004/0105161 A1* | 6/2004 | Tatum et al. ................... 359/634 |
| 2005/0224692 A1* | 10/2005 | Tsuchiya et al. ........... 250/201.3 |
| 2006/0033988 A1* | 2/2006 | Mikuriya et al. ............. 359/385 |
| 2008/0241065 A1* | 10/2008 | Benaron et al. ................ 424/9.1 |

FOREIGN PATENT DOCUMENTS

| DE | 196 33 185 | 10/1997 |
| DE | 196 49 605 | 6/1998 |
| DE | 103 61 176 | 7/2005 |
| DE | 10 2005 054 184 | 5/2007 |
| EP | 1 093 001 | 4/2001 |
| JP | 2003 195177 | 7/2003 |
| JP | 2005 010296 | 1/2005 |
| WO | WO 2006/072886 | 7/2006 |

* cited by examiner

*Primary Examiner* — Alessandro Amari
(74) *Attorney, Agent, or Firm* — Frommer Lawerence & Haug LLP

(57) ABSTRACT

The invention is directed to a multispectral illumination device for a microscope or for a reader. According to the invention, the illumination device comprises at least three receptacle positions for lighting modules and at least one receptacle position for coupling modules, the mechanical devices for connecting the lighting modules or coupling modules at the receptacle positions to the illumination device being designed in such a way that the lighting modules or coupling modules can be easily changed. Further, the receptacle positions are arranged in such a way that, with suitable selection of the lighting modules and coupling modules, all individual spectra of the lighting modules in a total spectrum are available simultaneously at the output of the illumination device.

11 Claims, 8 Drawing Sheets

MULTISPECTRAL LIGHTING APPARATUS

The present application claims priority from PCT Patent Application No. PCT/EP2007/008693 filed on Oct. 6, 2007, which claims priority from German Patent Application No. DE 10 2006 048 0554.6 filed on Oct. 11, 2006, the disclosure of which is incorporated herein by reference in its entirety.

BACKGROUND OF THE INVENTION

1. Field of the Invention

The invention is directed to a multispectral illumination device for a microscope or for a reader.

2. Description of Related Art

An important application for illumination devices is in arrangements for imaging and examination which are provided for generating images of an object or sample to be examined. Typical examples of such imaging devices are microscopes, particularly microscopes with widefield optics which image a given area of the sample to be imaged or examined. Fluorescence examination plays a special role in the optical examination of samples. In this case, the sample is irradiated by an excitation beam with a suitable excitation spectrum which is selected depending on one or more fluorescent dyes. When these fluorescent dyes are found in the sample, they interact with the excitation radiation and emit fluorescent radiation that is characteristic for the dye. Detection of the sample is made possible in this way. Not only the presence of fluorescent dyes but their concentration and spatial arrangement can also be determined.

Nanoparticles, for example, quantum dots, or other dyes which fluoresce in at least one wavelength can also be used instead of fluorescent dyes.

Light sources such as mercury arc lamps or xenon arc lamps are conventionally used in order to excite many different fluorescent dyes or nanoparticles. These light sources have a broad emission spectrum which extends from ultraviolet to near-infrared. The selection of the excitation spectrum required for a dye is usually carried out in microscopes through a set of filters, a so-called excitation filter, a beamsplitter, and an emission filter. Excitation filters and beamsplitter filters are selected in such a way that they pass or reflect the portion of the spectrum of the light source that is required for exciting the dye in the sample. The fluorescent radiation which is then emitted by the sample passes through the beamsplitter and the emission filter, which causes a further suppression of scattered excitation light. This combination of filters provides for improved contrast in a fluorescence image. Depending on the arrangement of the beam path in the microscope, the beamsplitter can also be omitted.

Often, filter sets with only one wavelength band are used in fluorescence experiments to excite the fluorescent dye. However, there are also multi-bandpass filter sets which make it possible to observe a fluorescent sample in multiple colors simultaneously or to change spectral regions in rapid sequence. Accordingly, a multicolored impression of the sample can be generated in the experiment, which allows different parts of the sample to be highlighted in color simultaneously. At the present time, multi-bandpass filter sets with two, three, or four transmission bands are available for fluorescence microscopy. These filters are called double bandpass filters, triple bandpass filters and quad bandpass filters. Triple bandpass filters and quad bandpass filters in particular are used, e.g., in FISH (fluorescence-in-situ hybridization) experiments. In such experiments it is desirable to be able to change quickly between all spectral regions of the light source or for all spectral regions of the light source to be available simultaneously.

More recently, light emitting diodes (LEDs) have been used for illumination in fluorescence microscopy. They have a substantially longer lifetime than arc lamps and offer optical emission outputs comparable to those of arc lamps in some spectral regions. Additional advantages are that they generate less heat, have higher electrical to optical efficiencies, faster switching speed and a narrower emission spectrum. Fast switching speeds of the illumination device are advantageous, for example, in experiments in which a microscopic object is tracked and in experiments for fast measurement of concentrations of dyes (ratio imaging). Accordingly, for digital recording of processes, processes requiring image frequencies above 50 Hz can be imaged.

At present, high-power light emitting diodes are available in virtually all relevant wavelength ranges for fluorescence microscopy. An overview is given in "Handbook of biological confocal microscopy" (third edition, Springer 2006, pages 126 ff.). Currently, optical power outputs in the range of several 100 mW are already achieved, and the spectral half-intensity width is in the range of 5 nm to 40 nm.

At the current time, there are no high-power light emitting diodes available in the ranges from 405 nm to 445 nm and 550 nm to 580 nm, in particular.

Typical spectral half-intensity widths of the spectral curves (absorption and emission) of fluorescent dyes are typically around 30 nm.

With regard to simultaneous multicolored illumination of fluorescent samples by a plurality of LEDs, the spatial and spectral coupling of the light radiation emitted by the respective LEDs is particularly important. Because of the narrow emission spectra of the LEDs, diffractive optics are also suitable for this purpose. With spectral coupling by means of diffractive elements, broadband light sources would be spatially blurred because their dispersion is dependent upon wavelength.

US20050224692 describes a microscope with an illumination device having a plurality of arrangements for coupling different-colored LEDs. The coupling of the LEDs by a cemented multiple-prism, dichromatic mirrors, an individual prism, and a grating is described. The coupling of three LEDs with a fixed emission spectrum is described. However, since LEDs have narrow emission spectra, an arrangement of this kind covers only part of the spectrum for fluorescence experiments. The description does not address expanding the available spectral region of the illumination device by exchanging individual LEDs and, as the case may be, coupling optics for LEDs of another spectrum in a modular manner.

DE102005054184 describes a multispectral illumination device in which lighting means such as LEDs are coupled together in a treelike structure by dichromats. The unit comprising lighting means and associated means for beam shaping and spectral shaping (collimation and filtering) along with the mechanical mounting of these components will be referred to hereinafter as a lighting module. Without loss of generality, the lighting means themselves can in turn comprise a plurality of light sources, for example, an array of LEDs. Without loss of generality, let the spectral half-intensity width of an individual spectrum of a lighting module be less than 40 nm. Means arranged downstream for beam coupling of the lighting modules will be referred to hereinafter as coupling modules. The lighting modules in DE102005054184 preferably comprise at least one LED, a filter and collimating optics which serve for spectral shaping and beam shaping of the light radiation emitted by the LEDs.

The total spectrum of the illumination device is composed of the individual spectra of the lighting modules whose emission radiation outputs can be adjusted independently from one another. In particular, all of the individual spectra are available simultaneously at the output of the illumination device. As has already been described, light emitting diodes typically have spectral half-intensity widths in the range of 5 nm to 40 nm. To make use of the above-described advantages of LEDs in fluorescence microscopy, an LED-based multi-spectral illumination device would have to have a large quantity of different-colored LEDs which, together, would cover virtually the entire spectral range of visible and near-infrared light. Accordingly, at least ten different-colored LEDs would be required just for complete coverage of the visible spectral region from about 350 nm to 700 nm. Obviously, an illumination device comprising this many LEDs would be complicated and expensive to build. Further, the space requirement for this is large and space would be taken up in the laboratory. DE102005054184 suggests extending the tree structure in order to expand the spectral coverage. An expansion of this kind involves a more complicated design of the illumination device because more lighting modules and more coupling modules would have to be accommodated in the illumination device.

WO2006072886 describes an illumination device for a transmitted-light fluorescence microscope in which individual lighting modules comprising, respectively, an LED, optics and a filter are coupled into the microscope by a mechanically exchangeable beamsplitter in a coupling module. The lighting modules can be detached from the coupling module individually and exchanged. The described illumination device only allows two individual spectra of the three lighting modules to be coupled. In order to change to the third lighting module, the coupling module must be re-plugged. Accordingly, a maximum of two individual spectra of the lighting modules is available in the microscope at one time. An expansion to three or more lighting modules whose individual spectra are present simultaneously at the output of the illumination device is impossible by nature of the design.

SUMMARY OF THE INVENTION

Against this background, it is the object of the present invention to provide a multispectral illumination device for a microscope or reader which makes possible simultaneous illumination with all individual spectra, in which an individual spectrum can be changed in a simple manner for experiments with more than two fluorescent dyes, and in which the illumination device is constructed compactly at the same time.

According to the invention, this object is met through the characterizing features of claim 1. Advantageous embodiments of the multispectral illumination device are indicated in the independent claims.

One idea of the invention is to provide a limited quantity of receptacle positions for lighting modules in the illumination device instead of accommodating all possible lighting modules but, in return, to ensure that these lighting modules can be exchanged in a modular manner. Therefore, the multispectral illumination device according to the invention comprises at least three receptacle positions for lighting modules and at least one receptacle position for a coupling module for coupling the light emitted by the lighting modules. Lighting modules can be connected to the illumination device at the receptacle positions for lighting modules by means of mechanical devices provided for this purpose. This also applies in a corresponding manner for the coupling modules at the receptacle positions for coupling modules. The mechanical devices can be mechanical holders, flanges, rotary threads, or other devices. The mechanical devices at the receptacle positions are constructed in such a way that the lighting modules or coupling modules can easily be detached from them.

When the receptacle positions for lighting modules are occupied by lighting modules with different individual spectra, all of the individual spectra are available simultaneously at the output of the illumination device, according to the invention, by means of the correspondingly designed and arranged coupling modules. In particular, as a result of the illumination device according to the invention, fluorescence experiments with the multi-bandpass filters mentioned above can be adapted and carried out. In particular, if necessary, missing wavelength ranges can be retrofitted by the user for an experiment. Depending on the user's budget, the illumination device according to the invention can also initially be outfitted with fewer lighting modules than there are available receptacle positions. When more than three fluorescent dyes are used in an experiment, crosstalk occurs because of the width of their excitation spectra and emission spectra. Crosstalk refers to the overlapping of the excitation spectra and/or emission spectra of the fluorescent dyes. In this case, these fluorescent dyes can no longer be excited individually and must be separated subsequently by techniques such as spectral unmixing when evaluated. Therefore, only two to three different dyes are used in many fluorescence experiments. In this case, the modular illumination device according to the invention makes the suitable configuration of lighting modules and coupling modules available for any experiment.

In an advantageous further development of the invention, the optical components of the coupling modules are dichromatic mirrors, gratings, prisms, or other diffractive optics or a combination of these optics. Coupling by means of diffractive optics offers the advantage that fewer coupling modules are needed because the coupling can already be effected by means of optics. On the other hand, dichromatic mirrors make possible a compact construction in which the lighting modules need not be readjusted after changing to a different lighting module.

The lighting modules can advantageously be outfitted with means for beam shaping and/or spectral shaping. Diffractive optics and/or lens arrays and/or lenses are particularly suitable means for beam shaping.

Suitable means for spectral shaping are optical filters, which additionally limit the individual spectrum of a lighting module.

In another advantageous embodiment of the invention, the receptacle positions for the lighting modules and coupling modules are outfitted with an interlock which switches off all of the lighting modules of the illumination device when a lighting module or coupling module is removed. This construction offers protection against eye injury when using high-power light emitting diodes. Therefore, no lighting module can emit light when it is not arranged in the receptacle position provided for it.

In another embodiment of the invention, the lighting modules and coupling modules of the multispectral illumination device are located in a common housing. In this way, the illumination device is protected from dust in a simple manner because this illumination device does not have as many mechanical interfaces and apertures. Further, the lighting modules and coupling modules are protected against misalignment due to unintentional contact.

Further, an interlock can advantageously be arranged at the housing cover of the illumination device and switches off all of the lighting modules when the housing is opened.

In another embodiment of the invention, the lighting modules can be switched on and off independently from one another and the emission radiation outputs of the lighting modules can be adjusted independently from one another. In this way, the illumination device can simultaneously address one or more color channels of the sample selectively through an electronic control and, beyond this, can adjust the relative intensity of its channels independently. Accordingly, in an advantageous manner, the different spectral excitation efficiency of dyes in the fluorescence sample can be compensated electronically and the different colors of the sample can be adjusted during observation.

Light emitting diodes are particularly preferred for use as lighting means in the lighting modules because they have a spectral half-intensity width roughly corresponding to the half-intensity width of fluorescent dyes. An efficient excitation can be achieved when the excitation spectrum of the fluorescent dye and the individual spectrum of a high-power light emitting diode are adapted in a corresponding manner. Further, the small spectral width of the emission spectra of LEDs allows them to be spectrally coupled by means of dispersive elements. However, laser diodes are also advantageous as lighting means because they possess a very high spectral luminance and accordingly make possible a selective excitation of a fluorescent dye in selected experiments.

Without loss of generality, the lighting means of the lighting modules can be provided with means for frequency conversion and/or coherence destruction. The emission of an LED or laser diode can be shifted to a different wavelength range by means of frequency conversion, e.g., through a dye. At the same time, the coherence which is disruptive in some experiments in widefield microscopy is destroyed.

Particularly to cover the spectral gaps of the high-power light emitting diodes with a modular illumination device, a further aspect of the invention consists in integrating a fiber-coupled, broadband light source such as a mercury arc lamp, xenon arc lamp or metal vapor arc lamp in the illumination device instead of a lighting module. In this case, the lighting module is replaced by a holding module for the fibers and other optics as well as filters for adapting the light radiation exiting from the fibers. For example, a missing spectral region of the illumination device can be substituted by adapting the filter of the fiber-coupled light source and corresponding coupling modules.

Without loss of generality, the fiber-coupled light source can also take the place of a plurality of lighting modules when it has internal means for the spectral splitting of the broadband light radiation emanating from it and for coupling these spectral components into different fibers.

Further, it is desirable to change easily between an LED-based illumination and illumination by a broadband high-pressure arc lamp. This is particularly advantageous when the sample emits only a weak fluorescence signal and the microscope or reader requires adjustment to the sample. In this case, high-pressure arc lamps are preferred over high-power light emitting diodes because of their higher spectral power output.

According to the invention, a displaceable prism or a swivelable mirror or other switching optics are arranged in front of the output of the illumination device. The optics can be inserted in the beam path electively either manually or by motor and the various operating modes thereof can be established.

In a preferred variant of the invention, the illumination device is outfitted with four receptacle positions for lighting modules. Limiting to four receptacle positions is advantageous because sophisticated experiments can still be carried out with four wavelength regions as when using quad band filters, but the illumination device can also be designed compactly at the same time. The compact construction is made possible in particular when the modules are arranged in a binary tree structure.

An advantageous construction of the four-channel illumination device can be achieved according to the invention through a suitable choice of dichromats. Accordingly, it is advantageous to divide the lighting modules into color regions that are located, respectively, in a cohesive spectral region. Longpass filters with a slope at the point of transition from one color region to the next are advantageous for coupling the LEDs comprising these color regions. When selecting longpass filters of this kind, the lighting modules in the color regions can be exchanged without changing the coupling modules.

Because of the limited quantity of lighting modules in the multispectral illumination device, it may be necessary in some cases to make available more individual spectra simultaneously at the output of the illumination device. According to the invention, this can be achieved in that a plurality of illumination devices are coupled together in turn by suitable optics for coupling. For example, it is conceivable that a first illumination device covers the spectral range from 350 nm to 500 nm and another illumination device covers the spectral range from 500 nm to 650 nm. The two illumination devices can then simply be coupled together by means of a suitably arranged dichromat and jointly coupled into the microscope or reader. According to the invention, an illumination device of the kind mentioned above has provisions for a mechanical and optical coupling of a plurality of illumination devices.

Further, connecting the illumination device to different types of microscopes requires different adapting optics which provide for coupling the light of the illumination device into the microscope in an optimal manner. In particular, this relates to the position of the field diaphragm plane and aperture diaphragm plane.

Instead of integrating adapting optics of this kind in the illumination device in a fixed manner, separate intermediate adapters with optics are provided for this purpose according to another aspect of the invention. These adapters have the typical mechanical interfaces for microscopes and are optimized for the respective type of microscope.

Although limiting to four illumination channels is particularly advantageous, it may be necessary in some cases for the illumination device to provide more wavelength bands and to change quickly between them. Therefore, according to another aspect of the invention, the illumination device is itself designed to be modular so that a plurality of illumination devices can be coupled together. This can be achieved, for example, by providing an exchangeable dichromat constructed as a longpass mirror at the output of the illumination device. For example, when a first illumination device provides the wavelength ranges from 350 nm to 500 nm, the wavelength range from 500 nm to 650 nm, for example, can be covered by another illumination device. The coupling is carried out in the first illumination device by a dichromat which is a longpass filter with a slope at 500 nm. Without loss of generality, a plurality of illumination devices can be coupled together in this way.

The illumination devices described above are suitable for fluorescent illumination of samples. In fluorescence microscopy, a distinction is made with respect to incident fluorescence in which the excitation light impinges on the sample from the same side from which the sample is observed. In transmitted-light fluorescence which is used in more expensive microscope systems, the sample is irradiated by transmitted light with illumination and observation taking place from opposite sides. A drawback of transmitted-light fluorescence consists in that the excitation radiation impinges on the emission filter at full intensity and, further, the excitation of the sample is dispersed to varying degrees, weaker and stronger, in thick samples. However, LEDs in particular are especially suited to transmitted-light fluorescence because their spectrum is narrow compared to the high-pressure arc lamps which are used otherwise. The excitation light can be favorably suppressed from the observation beam path joining the sample with the detector or observer by high-quality filters. A drawback of transmitted fluorescence illumination from a safety standpoint is that the full power of the light source strikes the observer directly if the fluorescence filter is unintentionally removed from the illumination and observation beam path. In mercury arc lamps conventionally used in fluorescence microscopy, this output would be up to 100 W light power which could cause severe injury to the eye. LED-based light sources on the other hand have the advantage in transmitted fluorescence illumination that, as a rule, only one lighting module with one wavelength band whose light power is in the range of several 100 mW maximum is switched on.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

Figure 1:
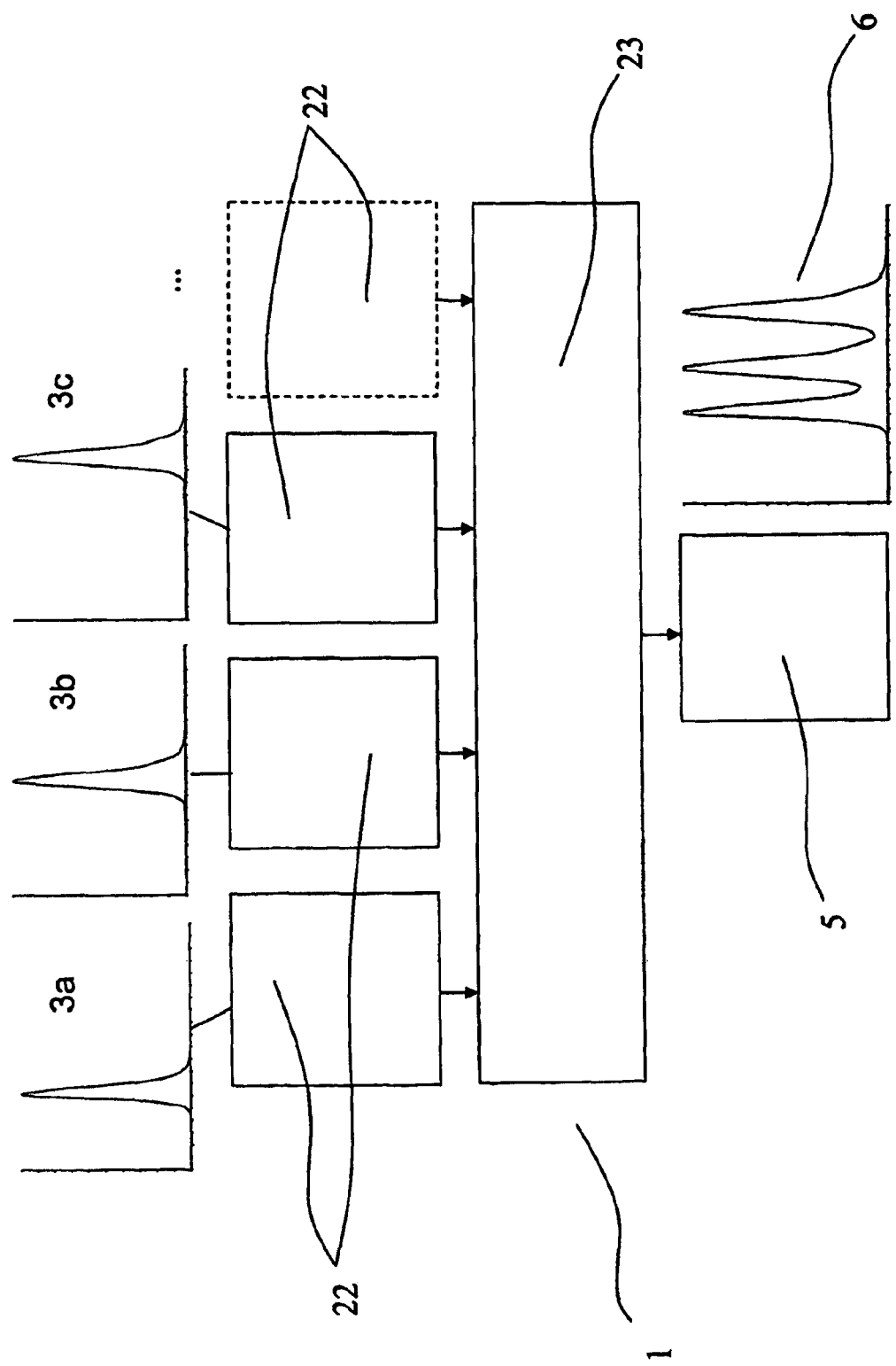
FIG. 1 is a schematic view of a multispectral illumination device according to the invention having at least three receptacle positions for lighting modules and at least one receptacle position for a coupling module.

The multispectral illumination device 1 according to the invention is shown schematically in FIG. 1. The at least three receptacle positions for lighting modules 22 and at least one receptacle position for coupling modules 23 make it possible to couple different individual spectra 3a-3c. By suitably selecting the lighting modules and coupling modules, not shown, all individual spectra 3 of the lighting modules in a total spectrum 6 are available simultaneously at the output of the illumination device 5. The individual spectra 3 can be switched on and off independently from one another selectively by the control electronics, not shown, of the lighting modules or by shutters. Further, the emission radiation outputs of the lighting modules can be adjusted independently from one another so that there is a high flexibility in spectral emission for the resulting total spectrum 6. In particular, this coupling makes it possible to change quickly between different individual spectra electronically. If the user wants to excite a different fluorescent dye efficiently by means of the multispectral illumination device for an experiment, this can be achieved by exchanging one or more lighting modules and thus adapting the light source to the experiment in an optimal manner.

Figure 2:
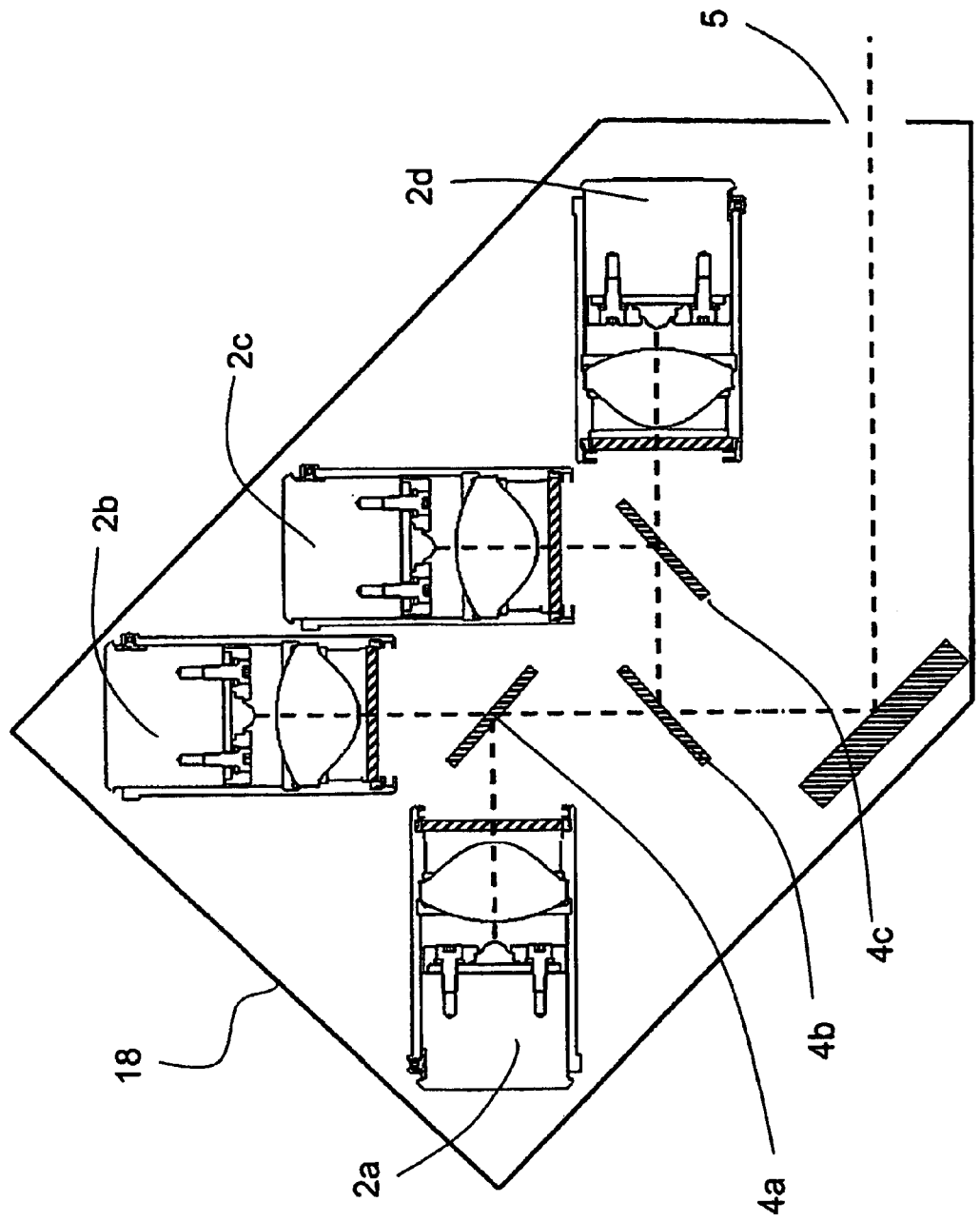
FIG. 2 shows an embodiment example of a multispectral illumination device with coupling modules comprising dichromatic beamsplitters.

FIG. 2 shows a first embodiment example of the invention. In the present case, the four lighting modules 2a-2d of the multispectral illumination device are accommodated in a common housing 18. The coupling modules 4a-4c are shown without a holder. The optics of the coupling modules are dichromatic mirrors, each of which is tuned to the individual spectra of the lighting modules 2a to 2d preceding it. When lighting module 2a, for example, is exchanged for a lighting module with a different individual spectrum, coupling module 4a, as the case may be, is exchanged for a suitable coupling module. It should be noted that when coupling by means of dichromatic mirrors the position of the lighting modules need not be readjusted with respect to the beam path when changed. This advantage facilitates changing the lighting modules.

Figure 3:
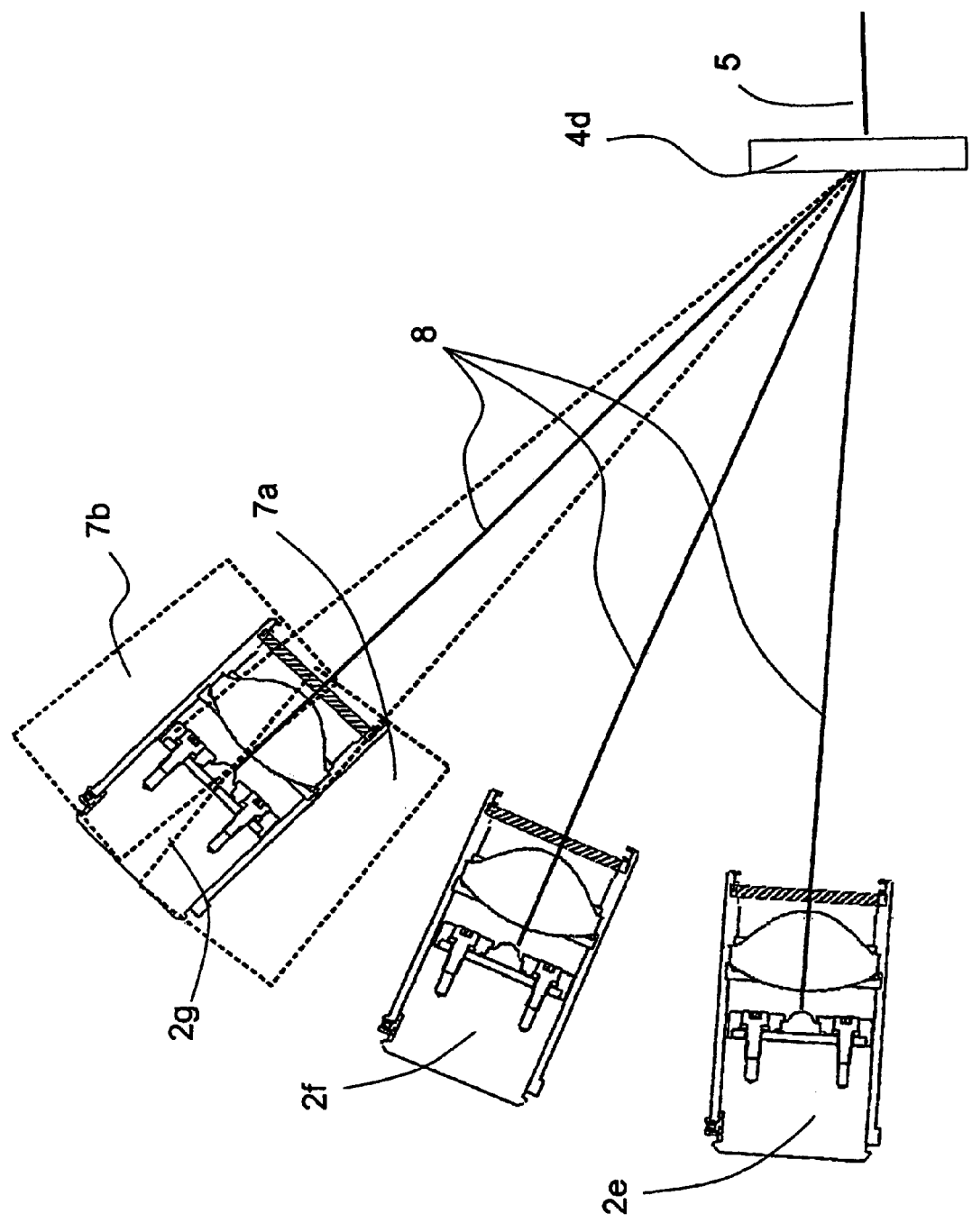
FIG. 3 shows another embodiment example of a multispectral illumination device with a coupling module containing diffractive optics for spectral coupling.

FIG. 3 shows another embodiment example of the invention. In this case, the lighting modules 2e-2g are spectrally coupled by means of a coupling module 4d which comprises diffractive optics. The center rays of the beam paths are designated by 8. Therefore, because of the wavelength-dependent effect of diffractive optics, the position of a lighting module must be adapted with respect to the diffractive optics when changing a lighting module. Therefore, two additional positions 7a and 7b are indicated by way of example in the drawing for a lighting module 2g. Position 7a would be chosen, for example, when the center wavelength of the individual spectrum of the new lighting module lies below that of the old lighting module. The reverse would apply in a corresponding manner when the center wavelength lies above that of the old lighting module. Without loss of generality, this effect can be exactly reversed depending on the mathematical sign of the dispersion of the diffractive optics. Compared to the first embodiment example in FIG. 2, fewer coupling modules and optics contained therein are required for this construction. In return, exchanged modules must be readjusted with respect to the beam path in order to make optimal use of the optical output emitted by them. Further, it will be readily appreciated that a minimum lateral distance between the lighting modules must be maintained to introduce exchanged modules at positions 7a and 7b and, because of the structural dimensions of the lighting modules, the distance between the lighting modules and the coupling module 4d will be large.

Figure 4:
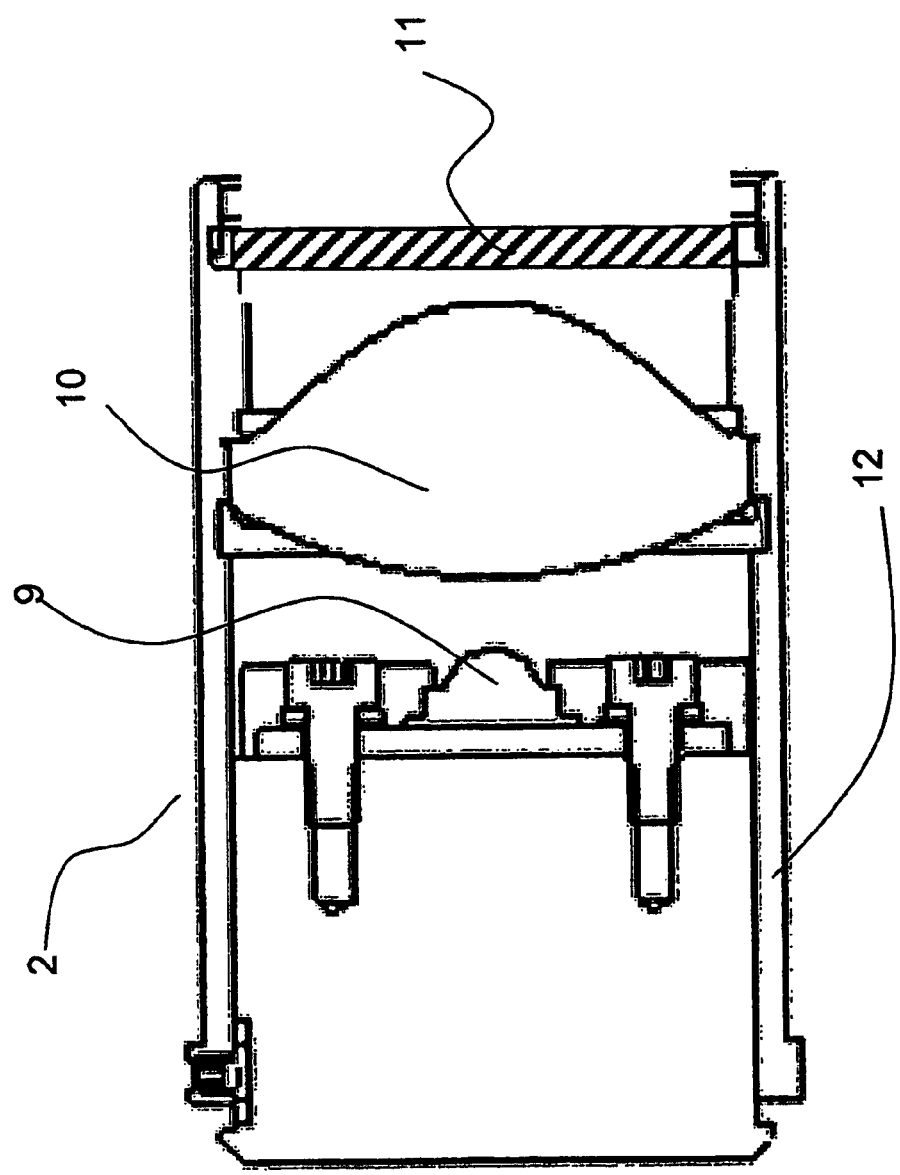
FIG. 4 shows the construction of a lighting module by way of example.

FIG. 4 shows the construction of a lighting module 2 by way of example. It comprises lighting means 9, optics for beam shaping 10, and optics for spectral shaping 11. The individual components are held in a common housing 12. It is particularly advantageous when the lighting modules are chromatically corrected so that they can be placed in any desired position of the illumination device without having to correct their position in direction of the optical axis leading from the lighting means to the output of the illumination device. This can be achieved by displacing the beam-shaping optics 10 in a suitable manner with respect to the lighting means 9. The effect of the optics 10 which is generally wavelength-dependent is made use of in this case. In an advantageous manner, the beam-shaping optics 10 comprise a short focal-length lens so that they can collimate a large proportion of the radiation emitted by the lighting means in all spatial angles. The spectral shaping optics 11 are preferably a bandpass filter adapted to the emission spectrum of the lighting means 9. For example, the long tail of the spectrum of a light emitting diode can be suppressed by means of this filter in order to improve the contrast of the image in a fluorescence experiment with a plurality of dyes.

Figure 5:
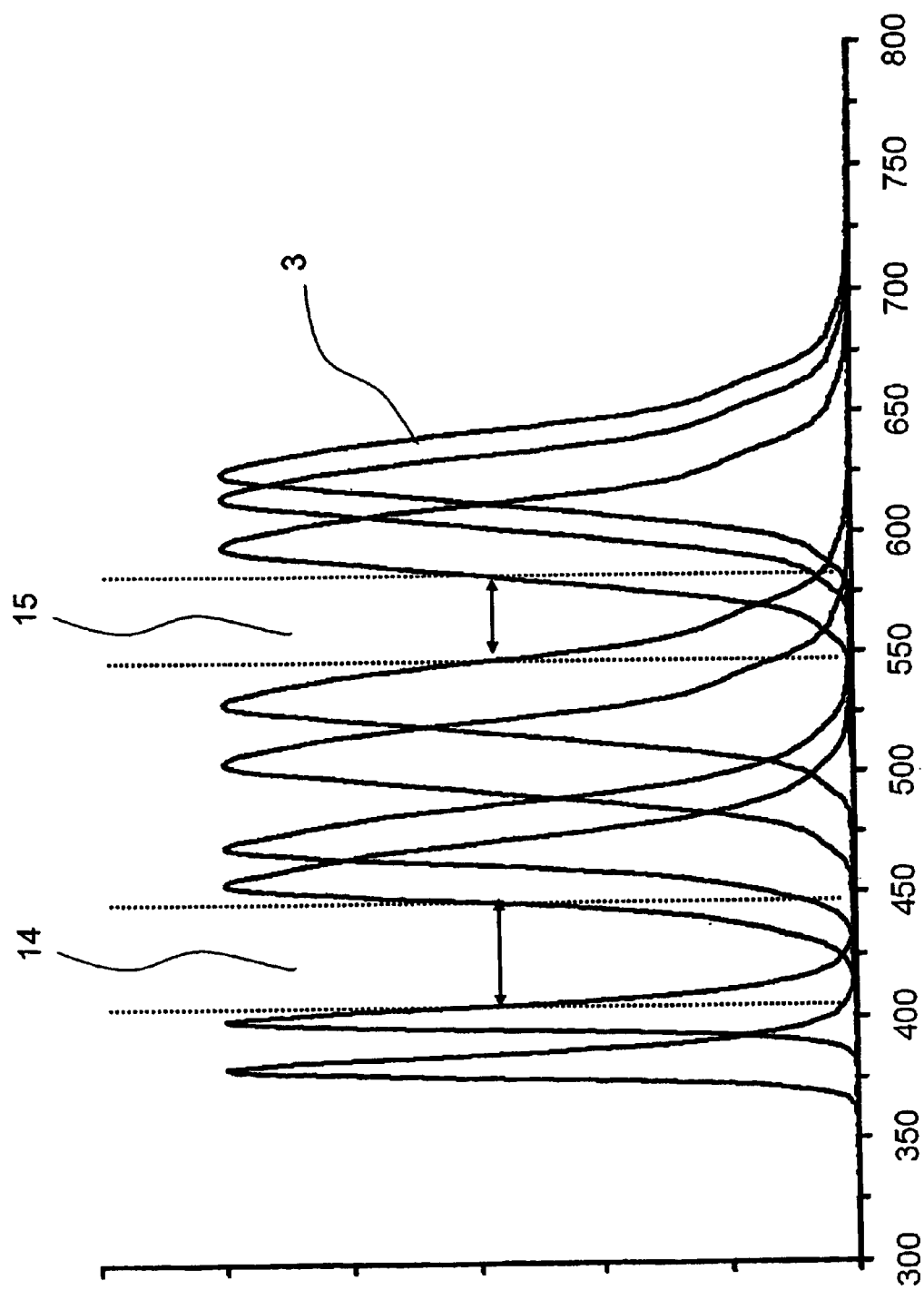
FIG. 5 shows normalized emission spectra of available high-power light emitting diodes and gaps in the availability of high-power light emitting diodes.

FIG. 5 shows a selection of individual spectra 3 of high-power light emitting diodes. The spectra are normalized across the wavelength. In particular, no high-power light emitting diodes having a strong emission radiation output are currently available in the ranges from 405 nm and 445 nm 14 and from 550 nm to 580 nm 15. However, the excitation spectra of some important fluorescent dyes lie precisely within range 15, so that it is desirable to also cover this spectral range with the multispectral illumination device. According to the invention, this is achieved by means of a broadband light source such as a mercury arc lamp, xenon arc lamp or metal vapor arc lamp which is incorporated into the illumination device instead of a lighting module. For this purpose, the lighting module can be replaced, for example, by a holding module for a fiber into which the radiation of the broadband light source is coupled and additional optics as well as filters for adapting the light radiation exiting from the fiber. Without loss of generality, the fiber-coupled light source can also be used in place of a plurality of lighting modules when it comprises internal means for spectral splitting of broadband light radiation emanating from it and for coupling these spectral components into different fibers. The partial spectra would advantageously cover regions 14 and 15 in FIG. 5.

Figure 6:
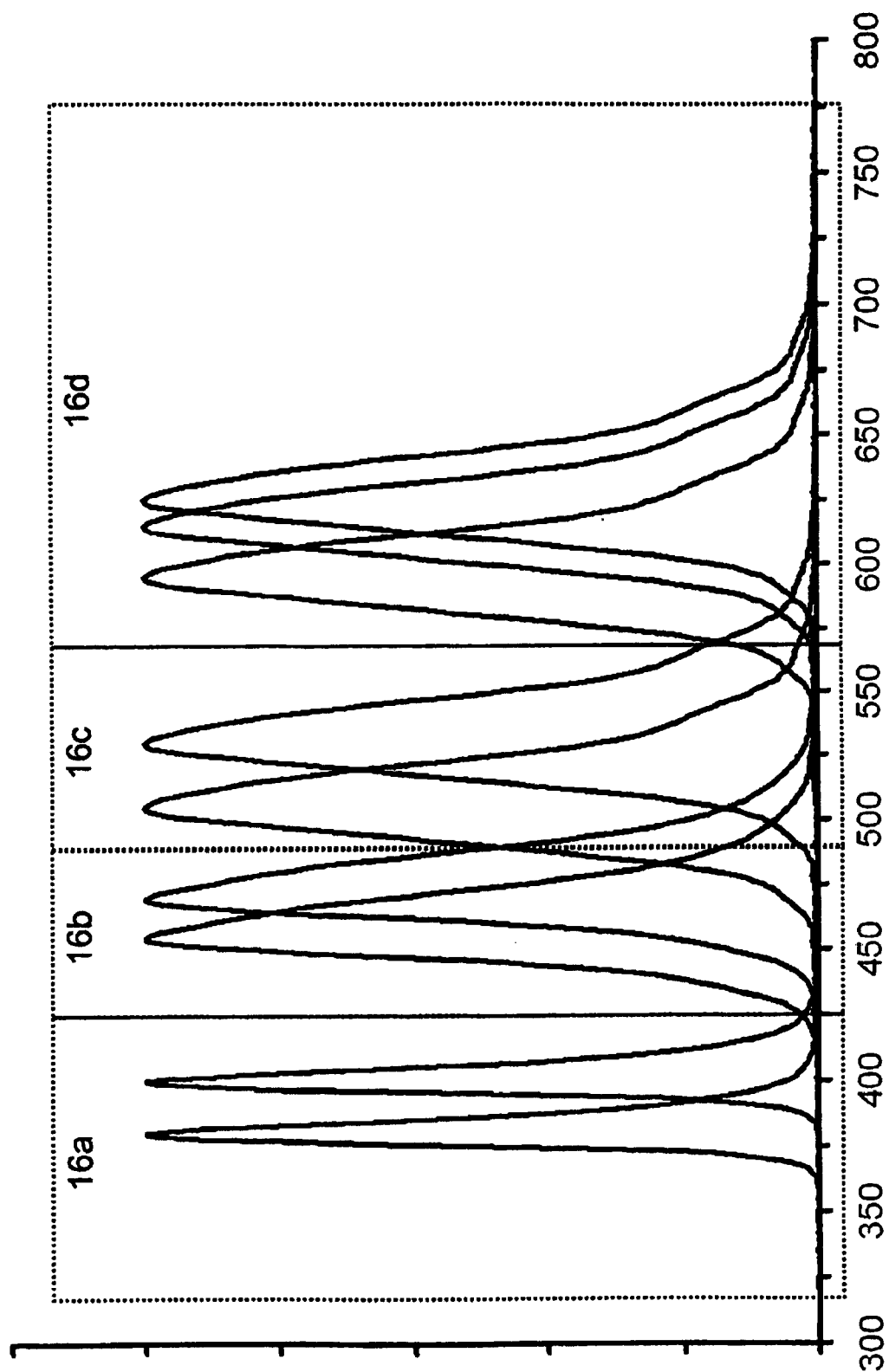
FIG. 6 shows the emission spectra of the lighting modules divided into different color bands.

FIG. 6 shows the dividing of the possible individual spectra of lighting modules of a multispectral illumination device into different color regions 16a-16d which do not overlap. Assuming that lighting modules of a color region need not be incorporated in the multispectral illumination device simultaneously, an economical illumination device can accordingly be provided with three dichromatic beamsplitters whose slopes lie exactly on the boundaries of the color regions and which are constructed as longpasses, because changing the lighting modules in a color region does not also require that the subsequent coupling modules be changed. In FIG. 6, longpass filters with a slope at about 425 nm, 485 nm and 570 nm are selected as dichromats.

Figure 7:
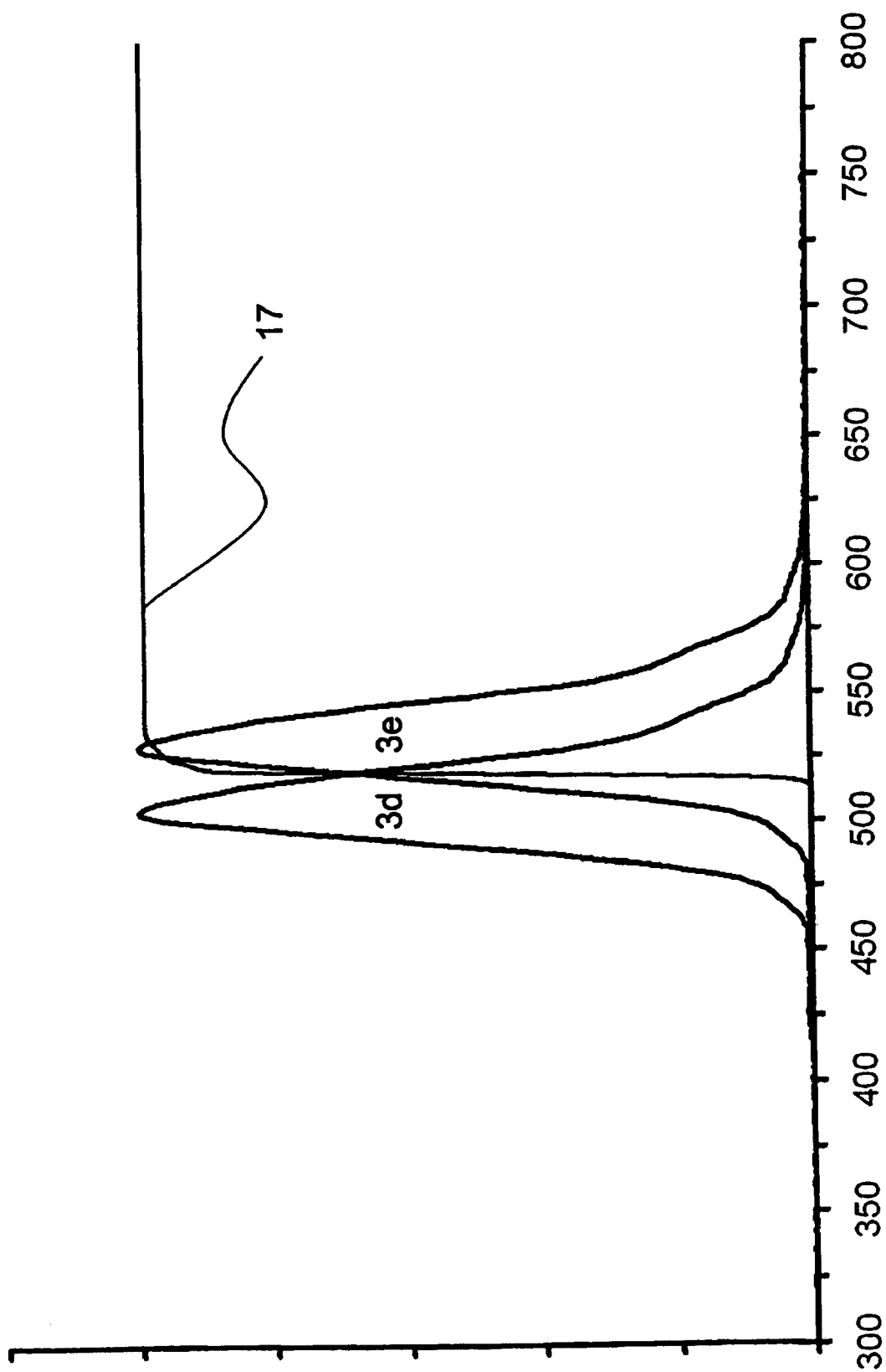
FIG. 7 shows the emission spectra of two high-power light emitting diodes and the reflection curve of a dichromatic beamsplitter for spectral coupling of the individual spectra.

However, if an experiment requires that two spectrally close dyes respond, the dichromatic beamsplitter must be adapted corresponding to FIG. 7. In this case, 3d and 3e are individual spectra of two lighting modules which are coupled with a dichromatic beamsplitter whose transmission curve 17 is shown. It is also clear from this diagram that the resulting individual spectra, not shown, are cropped in this case because, for example, individual spectrum 3e passes through the beamsplitter and loses the portion lying to the left of the slope at about 525 nm, while individual spectrum 3d loses the portion lying to the right of the slope when reflected at the beamsplitter.

Figure 8:
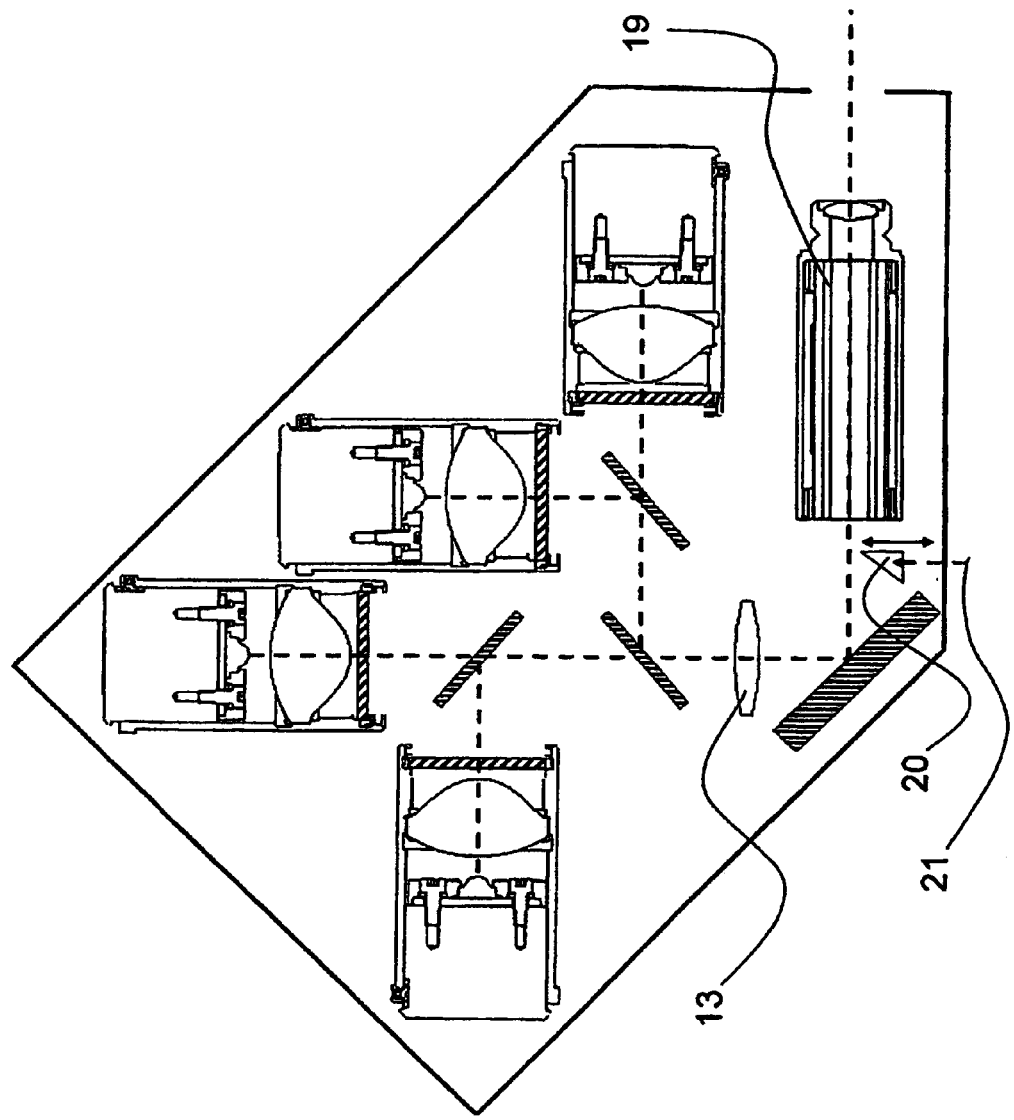
FIG. 8 shows another embodiment example of a multispectral illumination device with additional optical elements.

FIG. 8 shows another embodiment example of the invention. Additional optics are contained in this case in addition to the components already described with reference to FIG. 2. Accordingly, reference number 13 designates a lens for adapting the radiation emitted by the lighting modules at the entrance plane of an optical integrator rod 19 which is advantageously used for spatial homogenization of the light radiation at the output of the multispectral illumination device. Further, optics 20 are shown which can be inserted in the beam path of the illumination device manually or by motor. Accordingly, the light of a broadband light source 21, for example, can be coupled into the illumination device in a simple manner.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

REFERENCE NUMBERS 1 illumination device
2 lighting module
3 individual spectrum
4 coupling module
5 output of the illumination device
6 total spectrum
7 position
8 center rays of the beam paths
9 lighting means
10 (beam-shaping) optics
11 (spectral shaping) optics
12, 18 housing
13 lens
14, 15, 16 region (nm)
17 transmission curve
19 optical integrator rod
20 optics
21 (broadband) light source
22 lighting module
23 coupling module

The invention claimed is:
1. A multispectral illumination device for a microscope or reader comprising:
    four exchangeable lighting modules, each light module having a spectral region that is different from the spectral regions of the other light modules; and
    three exchangeable coupling modules, each with a dichromatic mirror for coaxial superimposition of the light radiation emitted by the lighting modules;
    wherein the dichromatic mirrors, which are designed as longpass filters, divide the entire spectral region into four color regions;
    wherein a lighting module lies in one of the four color regions, and the lighting modules and coupling modules are arranged in a binary tree structure;
    wherein, when exchanging one lighting module for another light module whose spectral region lies in a different color region, the dichromats of the coupling modules are adapted to the individual spectra of the lighting modules arranged in front of them; and wherein each longpass filter is selected in such a way that all individual spectra of the lighting modules in an entire spectrum are available simultaneously at an output of the multispectral illumination device.

2. The multispectral illumination device according to claim 1;

wherein each lighting module comprises at least one lighting means, at least one means for beam shaping, and/or at least one means for spectral shaping.

3. The multispectral illumination device according to claim 2;

wherein the means for beam shaping comprises diffractive optics and/or lens arrays and/or lenses; and wherein each means for spectral shaping comprises a filter.

4. The multispectral illumination device according to claim 1;

wherein interlocks, which switch off all of the lighting modules of the multispectral illumination device when any light module is removed, are provided at the receptacle positions for the lighting modules and coupling modules.

5. The multispectral illumination device according to claim 1;

wherein the lighting modules and coupling modules are contained in a common housing.

6. The multispectral illumination device according to claim 5;

wherein the housing is outfitted with an interlock which switches off the lighting modules when the housing is opened.

7. The multispectral illumination device according to claim 1;

wherein each lighting means of each lighting module comprises at least one LED.

8. The multispectral illumination device according to claim 1;

wherein one lighting means of one of the lighting modules is a laser diode.

9. The multispectral illumination device according to claim 1;

wherein at least one lighting module is replaced by a fiber-coupled, broadband light source.

10. The multispectral illumination device according to claim 1;

wherein a fiber-coupled light source is introduced into the beam path of the multispectral illumination device by mechanically or electrically switchable optics.

11. The multispectral illumination device according to claim 10;

wherein the switchable optics are a displaceable prism or a swivelable mirror.

* * * * *